United States Patent [19]
Feith et al.

[11] Patent Number: 5,730,418
[45] Date of Patent: Mar. 24, 1998

[54] MINIMUM FLUID DISPLACEMENT MEDICAL CONNECTOR

[75] Inventors: Raymond P. Feith, Rialto; David L. Ludwig, San Juan Capistrano; Timothy L. Truitt, Orange, all of Calif.

[73] Assignee: The Kipp Group, Ontario, Calif.

[21] Appl. No.: 724,180

[22] Filed: Sep. 30, 1996

[51] Int. Cl.⁶ ........................................ F16L 37/28
[52] U.S. Cl. ........................ 251/149.6; 251/149.1; 604/256; 604/905
[58] Field of Search ................ 251/149.1, 149.6; 604/905, 256

[56] References Cited

U.S. PATENT DOCUMENTS

| | | |
|---|---|---|
| 3,896,853 | 7/1975 | Bernhard . |
| 3,977,403 | 8/1976 | Patel . |
| 4,296,949 | 10/1981 | Muetterties et al. . |
| 4,346,703 | 8/1982 | Dennehey et al. . |
| 4,439,188 | 3/1984 | Dennehey et al. . |
| 4,449,693 | 5/1984 | Gereg . |
| 4,483,368 | 11/1984 | Panthofer . |
| 4,607,868 | 8/1986 | Harvey et al. . |
| 4,673,400 | 6/1987 | Martin . |
| 4,710,168 | 12/1987 | Schwag et al. . |
| 4,778,447 | 10/1988 | Velde et al. . |
| 4,819,684 | 4/1989 | Zaugg et al. . |
| 4,880,414 | 11/1989 | Whipple . |
| 4,915,687 | 4/1990 | Sivert . |
| 4,963,133 | 10/1990 | Whipple . |
| 4,991,413 | 2/1991 | Arnaldo . |
| 4,991,629 | 2/1991 | Ernesto et al. . |
| 5,031,675 | 7/1991 | Lindgren . |
| 5,122,123 | 6/1992 | Vaillancourt ............................ 604/192 |
| 5,125,915 | 6/1992 | Berry et al. . |
| 5,147,333 | 9/1992 | Raines . |
| 5,215,538 | 6/1993 | Larkin . |
| 5,224,515 | 7/1993 | Foster et al. . |
| 5,253,842 | 10/1993 | Huebscher et al. . |
| 5,267,966 | 12/1993 | Paul . |
| 5,284,475 | 2/1994 | Mackal . |
| 5,293,902 | 3/1994 | Lapierie . |
| 5,312,083 | 5/1994 | Ekman ............................... 251/149.1 |
| 5,312,377 | 5/1994 | Dalton . |
| 5,353,837 | 10/1994 | Faust . |
| 5,398,530 | 3/1995 | Derman . |
| 5,411,483 | 5/1995 | Loomas et al. . |
| 5,439,452 | 8/1995 | McCarty . |
| 5,442,941 | 8/1995 | Kähönen et al. . |
| 5,456,676 | 10/1995 | Nelson et al. . |
| 5,474,544 | 12/1995 | Lynn . |
| 5,501,426 | 3/1996 | Atkinson et al. . |
| 5,509,433 | 4/1996 | Paradis ............................... 251/149.1 |
| 5,569,235 | 10/1996 | Ross et al. ........................... 251/149.1 |

Primary Examiner—A. Michael Chambers
Attorney, Agent, or Firm—Richard L. Myers

[57] ABSTRACT

A device for transferring fluid with minimum fluid displacement includes a valve internal chamber adapted for receiving an actuator therethrough for facilitating introduction of fluid into the valve internal chamber. A biased member abuts against either a compressible gas or an ambient atmosphere, and is adapted for being moved by the actuator. Movement of the biased member results in displacement of either the compressible gas or the ambient atmosphere to thereby offset a displacement of fluid in the valve internal chamber that was introduced by insertion of the actuator into the valve internal chamber. A valve outlet port is adapted for outputting fluid from the valve internal chamber. The valve outlet port is configured in fluid communication with the valve internal chamber at all times, and is adapted for allowing fluid to freely flow between the valve internal chamber and the valve outlet port.

32 Claims, 3 Drawing Sheets

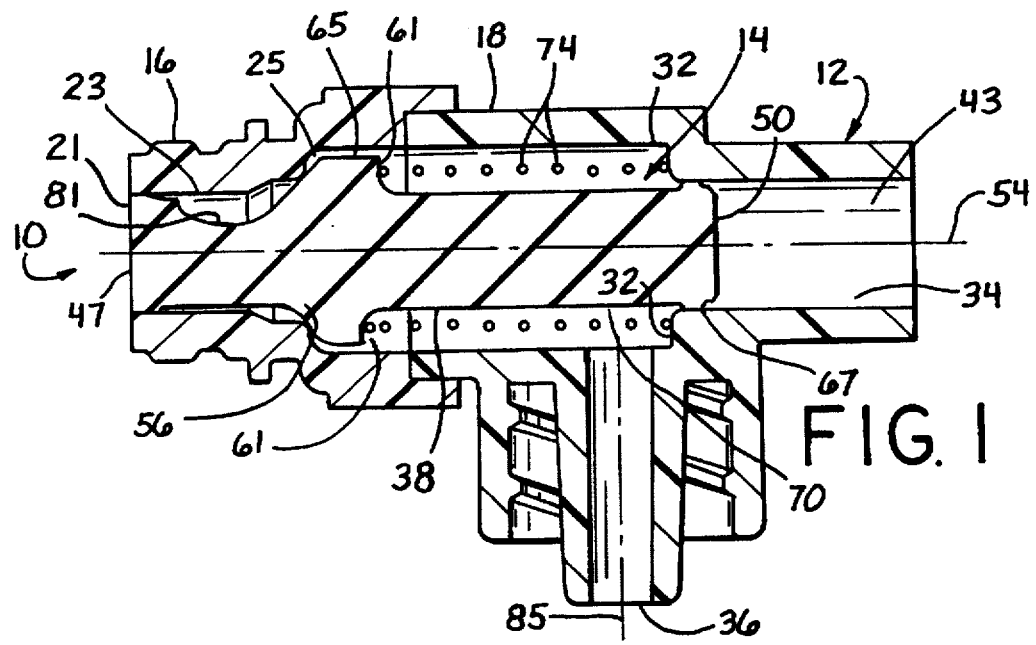
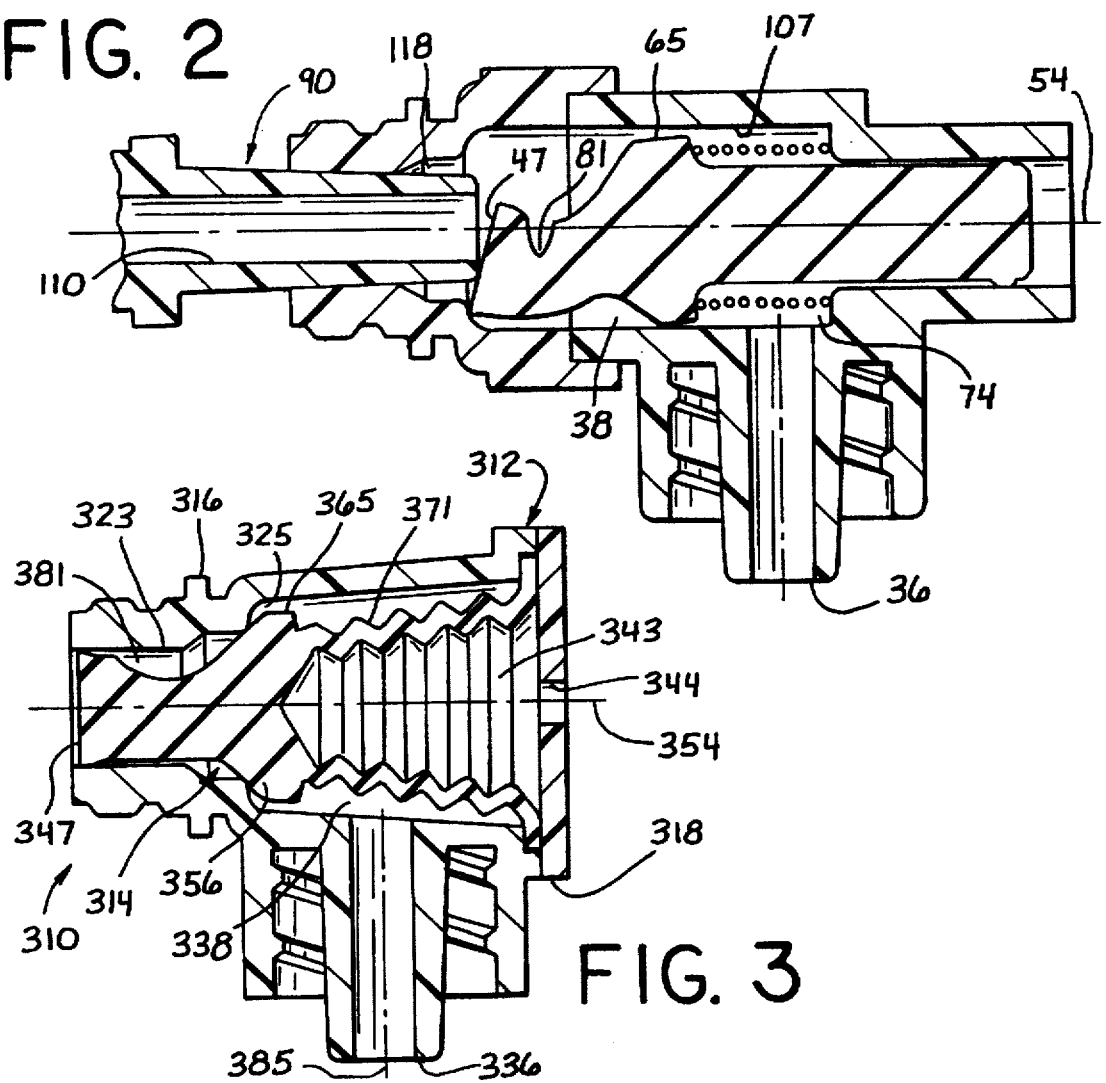

MINIMUM FLUID DISPLACEMENT MEDICAL CONNECTOR

BACKGROUND OF THE INVENTION

1. Field of the Invention

The present invention relates generally to devices for establishing connections in closed fluid systems where fluid displacement due to the connection process must be controlled and, more particularly, to devices for establishing connections to medical intravenous fluid lines for the purposes of adding fluids to or removing fluids from a patient's venus or arterial blood system, and for sampling or removing fluids from such fluid lines.

2. Description of Related Art

Aseptic medical connections have been widely used in the prior art in connection with intravenous fluid lines, blood access, hemodialysis, peritoneal dialysis, enteral feeding, drug vial access, etc. The general standard for many such aseptic medical connections has been to puncture an elastomeric diaphragm or septum, which has one side in contact with the fluid, with a sharpened hollow hypodermic needle. The use of such hypodermic needles has been gradually decreasing in the prior art, as a result of both safety and cost considerations associated with infectious disease acquired from needle sticks.

A phenomenon referred to as fluid displacement can occur whenever a connection is made between two closed fluid systems. When a hypodermic needle is inserted into an intravenous fluid tubing through a rubber (latex) injection site, fluid displacement occurs. Because the intravenous fluid is incompressible, a volume of fluid equal to the needle volume is displaced out of the intravenous tubing and into the patient's blood vessel, when the hypodermic needle is inserted into the injection site. This displacement of fluid from the intravenous tubing into the patient's blood vessel is referred to as antegrade flow. Similarly, when the hypodermic needle is withdrawn, an equivalent volume of blood will be drawn back, usually through the catheter, into the intravenous tubing. This retrograde flow can be harmful when the blood drawn into the end of the catheter remains stagnant for a long period of time. The stagnant blood tends to settle, and may begin to clot, thereby restricting flow through the catheter and possibly requiring insertion of a new intravenous catheter into the patient.

The phenomenon of retrograde flow is known to sophisticated medical practitioners, who may deliberately attempt to balance the retrograde flow and displacement by using a syringe to squeeze a last bit of fluid through the needle as the needle is being withdrawn from the latex septum. The success of this method, however, is highly variable and technique-dependent and, in any event, can only be employed when the device being disconnected is a needle. Many connections are from male Luers on ends of other intravenous tubing sets. The fluid displacement phenomenon described above can also occur in any closed fluid system, medical or not, where part of one of the connectors displaces volume into the system as the connector is actuated during coupling.

In addition to fluid displacement problems associated with hypodermic needle access intravenous connectors, many medical needle-free access devices create fluid displacement during actuation. Needle-free access devices employing blunt cannula "actuators," which penetrate a pre-slit rubber septum, and needle-free access devices activated by insertion of standard male Luer nozzles, often suffer from fluid displacement during actuation. In each of these cases, the actuator typically displaces fluid as it is inserted into the connector, creating antegrade flow. Also, when the actuator is removed from the connector, a volume within the connector must then be replaced by fluid within the intravenous tubing. If there is no other source (such as from an infusion container via a Y-connector), the replacement fluid will likely be the patient's blood, which will flow into the intravenous catheter.

The volume of fluid displaced during actuation in a case where a male Luer nozzle is used as the actuator, will often be approximately equal to the volume of the male Luer nozzle penetrating into the connector when coupled. This volume can vary substantially, based upon device design, materials, and the tolerances allowed for both male and female Luers. Displacement volumes can be 100 microliters or higher. A fluid displacement on the order of 50 microliters, for example, may seem very small but, in fact, can be significant. For instance, the fluid volume inside a one inch long 22 gauge intravenous catheter is only 6 microliters, and the volume of a one and a quarter inch 18 gauge catheter is 23 microliters. The volume displaced by inserting a 20 gauge needle to a depth of one inch is 24 microliters. Based upon the above dimensions, a catheter may be filled with blood by simply withdrawing a needle from an injection site. A displacement-free medical connector, or a minimum fluid displacement medical connector, or a self-flushing medical connector would attenuate or completely alleviate many of the problems associated with these prior art medical connectors.

SUMMARY OF THE INVENTION

The minimum displacement connector of the present invention includes an actuator and an internal chamber that is vented to the atmosphere. The present invention further includes a biased member that can be moved by the actuator to displace air out of the internal chamber while significant fluid is not displaced during actuation.

According to one feature of the present invention, a device for transferring fluid with minimum fluid displacement includes a valve internal chamber adapted for receiving an actuator therethrough for facilitating introduction of fluid into the valve internal chamber. A biased member abuts against either a compressible gas or an ambient atmosphere, and is adapted for being moved by the actuator. Movement of the biased member results in displacement of either the compressible gas or the ambient atmosphere to thereby offset a displacement of fluid in the valve internal chamber that was introduced by insertion of the actuator into the valve internal chamber. A valve outlet port is adapted for outputting fluid from the valve internal chamber. The valve outlet port is configured in fluid communication with the valve internal chamber at all times, and is adapted for allowing fluid to freely flow between the valve internal chamber and the valve outlet port.

According to another aspect of the present invention, a valve for transferring fluid includes an internal chamber that is in fluid communication with an outlet port. The internal chamber is adapted for accommodating an actuator therein. Insertion of the actuator into the internal chamber results in a positive fluid displacement within the internal chamber and, further, removal of the actuator from the internal chamber results in a negative fluid displacement within the internal chamber. The valve further includes an air chamber, and a biased member adapted for being moved into a portion of the air chamber upon insertion of the actuator and for being removed out of a portion of the air chamber upon removal of the actuator. Movement of the biased member into a portion of the air chamber results in a negative fluid displacement within the internal chamber which substantially compensates for the positive fluid displacement, and movement of the biased member out of a portion of the air chamber results in a positive fluid displacement within the internal chamber which substantially compensates for the negative fluid displacement, for a zero displacement within the internal chamber.

The biased member has a generally cylindrical shape and, according to one aspect of the present invention, includes a hollow, collapsible skirt which surrounds and defines the air chamber. Movement of the actuator into the internal chamber collapses the collapsible skirt and moves the biased member into a portion of the air chamber. According to another aspect of the present invention, a biasing member such as a spring can be disposed within the collapsible skirt, and movement of the actuator out of the internal chamber uncollapses the collapsible skirt and moves the biased member out of a portion of the air chamber under forces exerted by the spring. In one configuration of the present invention, an axis of the internal chamber is substantially perpendicular to an axis of the outlet port, and in another configuration of the present invention the axis of the internal chamber is substantially parallel to the axis of the outlet port. The valve may include an internal strut disposed within the collapsible skirt, where movement of the actuator into the internal chamber collapses the collapsible skirt for a predetermined distance until a portion of the biased member contacts the internal strut.

According to another aspect of the present invention, the biased member includes a hollow passage connecting the internal chamber to the outlet port. The hollow passage is surrounded by the air chamber, and is adapted to expand into a portion of the air chamber when the actuator is inserted into the internal chamber. The hollow passage is further adapted to contract and move out of a portion of the air chamber when the actuator is removed from the internal chamber. The air chamber is configured in fluid communication with an ambient atmosphere, and movement of the biased member into a portion of the air chamber results in displacement of air within the air chamber out of the air chamber and into the ambient atmosphere. The biased member further includes an annular member adapted for being secured to a wall of the internal chamber. The annular member serves as a biasing means for contracting the hollow passage and moving the hollow passage out of the air chamber when the actuator is removed from the internal chamber.

According to yet another feature of the present invention, a minimum fluid displacement self-flushing connector includes a valve internal member, and a valve inlet port adapted for receiving an actuator. The actuator includes a lumen for introducing fluid through the valve inlet port and into the valve internal chamber. The minimum fluid displacement self-flushing connector further includes a valve outlet port, which is adapted for outputting fluid from the valve internal chamber. The valve outlet port is in fluid communication with the valve internal chamber at all times, and is adapted for allowing fluid to freely flow into and out of the valve internal chamber. The minimum fluid displacement self-flushing connector further includes an air chamber and a plug adapted for being moved into a portion of the air chamber when the actuator is moved into the valve internal chamber. Movement of the plug into the air chamber results in a minimum displacement of fluid through the valve outlet port when the actuator is moved into the valve internal chamber. A displacement of air within the air chamber, resulting from movement of the plug into a portion of the air chamber, is approximately equal to a displacement of fluid within the valve internal chamber, resulting from movement of the actuator into the valve internal chamber. The valve inlet port includes an inlet port axis, and the air chamber is centered about the inlet port axis. The plug has a generally cylindrical shape which is also generally centered about the inlet port axis, and the plug is adapted for being moved from an inlet port closed position to an inlet port open position.

The actuator is adapted for moving the plug into the inlet port open position, where a distal portion of the plug is moved into a portion of the air chamber. The proximal portion of the plug is adapted for being pushed by the actuator from the inlet port closed position out of the valve inlet port and into the inlet port open position where the distal portion of the plug is positioned within a portion of the air chamber. The minimum fluid displacement connector may also include a spring, and the plug is adapted for being pushed by the spring from the inlet port open position to the inlet port closed position. Movement of the actuator into the valve internal chamber roughly corresponds to movement of the distal portion of the plug into a portion of the air chamber. Movement of the actuator into the valve internal chamber results in a displacement of fluid within the valve internal chamber that is compensated by movement of portions of the plug out of the valve internal chamber to thereby generate an approximately zero displacement within the valve internal chamber. The plug includes a primary shoulder seal adapted for contacting a valve seal of the minimum fluid displacement connector when the plug is in the inlet port closed position.

The primary shoulder seal is removed from contact with the valve seat when the plug is moved from the inlet port closed position to the inlet port open position. A first portion of the primary shoulder seal contacts an inner surface of the valve internal chamber when the plug is in the inlet port open position, and a second portion of the primary shoulder seal does not contact the inner surface of the valve internal chamber when the plug is in the inlet port open position. The inlet port open position of the plug facilitates a flow of fluid from the valve inlet port into the valve internal chamber, and between the second portion of the primary shoulder seal and the inner surface of the valve internal chamber into the valve outlet port.

The present invention, together with additional features and advantages thereof, may best be understood by reference to the following description taken in connection with the accompanying illustrative drawings.

BRIEF DESCRIPTION OF THE DRAWINGS

FIG. 1 illustrates a cross-sectional view of the minimum fluid displacement connector of the presently preferred embodiment in an unactuated configuration;

FIG. 2 illustrates a cross-sectional view of the minimum fluid displacement connector of the presently preferred embodiment in an actuated configuration;

FIG. 3 illustrates a minimum fluid displacement connector according to a first alternative embodiment;

DETAILED DESCRIPTION OF THE PRESENTLY PREFERRED EMBODIMENTS

Figure 4:
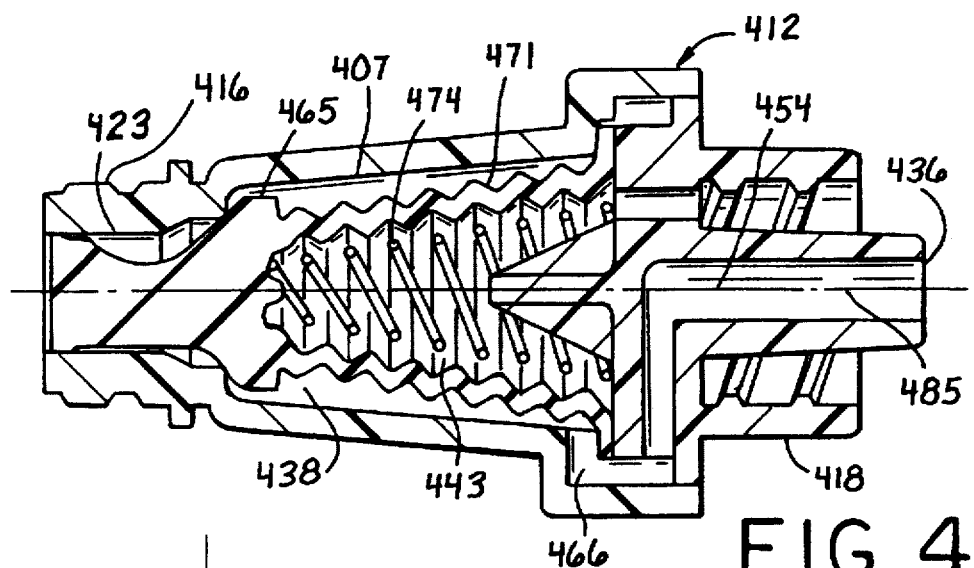
FIGS. 4 illustrates a minimum fluid displacement connector according to a second alternative embodiment.

Turning to FIG. 1, a minimum fluid displacement connector 10 is illustrated in cross-sectional view. The minimum fluid displacement self-flushing connector 10 comprises a valve housing 12 and a rubber valve plug 14 disposed within the valve housing 12. As presently embodied, the valve housing 12 comprises a valve cap 16 and a valve base 18. The valve cap 16 is secured to the valve base 18 using conventional means, such as solvent bonding, ultrasonics, spin welding, etc, and comprises a valve inlet port 21, a valve throat 23, and a valve seat 25. The valve base 18 comprises spring bases 32, a valve distal cylinder 34, and a valve outlet port 36. A valve internal chamber 38 is formed between the valve base 18 and the valve cap 16, and a vented air chamber 43 is formed within the valve distal cylinder 34. The valve base 18 and the valve cap 16 may comprise either metal or plastic, for example.

The rubber valve plug 14 comprises a generally cylindrical shape for slidably fitting within the valve internal chamber 38 and the vented air chamber 43 of the valve housing 12. The rubber valve plug 14 comprises a plug proximal portion 47 and a plug distal portion 50. The positioning of the plug proximal portion 47 may be flush or, may be sub-flush requiring use of a cap. An axis of the rubber valve plug 14 is generally aligned with an axis 54 of the valve throat 23 and the valve distal cylinder 34. The rubber valve plug 14 comprises a plug primary shoulder seal 56 adapted for abutting against the valve seat 25 of the valve cap 16. The rubber valve plug 14 further comprises plug spring bases 61, which in combination with the plug primary shoulder seal 56 form an enlarged diameter portion 65 of the rubber valve plug 14. Located near the plug distal portion 50 is a plug biased member 67 for sealingly sliding within the valve distal cylinder 34. A plug cylindrical portion 70 is disposed between the plug spring base 61 and the plug biased member 67. A metal or plastic spring 74 fits between the spring base 32 of the valve housing 12 and the plug spring base 61. Other biasing means may be employed in addition to, or as an alternative to, the metal spring 74.

A reduced diameter portion 81 of the rubber valve plug 14 is not centered about the axis 54. The reduced diameter portion 81 is presently configured to facilitate a clockwise pivoting action of the plug proximal portion 47 about the reduced diameter portion 81, when a force is applied to the plug proximal portion 47 in a direction toward the plug distal portion 50. (See FIG. 2.) An outlet port 36 of the valve housing 12 comprises an outlet port axis 85 that can be generally perpendicular or in line (parallel) to the axis 54.

Broadly speaking, the general concept of the minimum fluid displacement or self-flushing connector 10 of the presently preferred embodiment is to transfer fluid between the valve inlet port 21 and the valve outlet port 36. The plug primary shoulder 56 of the rubber valve plug 14 prevents fluid flow between the valve inlet port 21 and the valve outlet port 36, in the inlet port closed configuration. Further, in this inlet port closed configuration, the valve inlet port 21 is sealed from the valve internal chamber 38, but the valve internal chamber 38 is not sealed from fluid communication with the valve outlet port 36.

Turning to FIG. 2, an actuator 90 can be inserted into the valve inlet port 21 to thereby push the plug proximal portion 47 in the direction of the plug distal portion 50. The actuator 90 comprises a male Luer nozzle in the presently preferred embodiment. The actuator 90 pushes the plug proximal portion 47 out of the valve throat 23 and, simultaneously, causes the plug proximal portion 47 to slightly rotate relative to the reduced diameter portion 81 in the clockwise direction, as presently embodied. This slight rotation of the plug proximal portion 47, coupled with a general migration of both the plug proximal portion 47 and the reduced diameter portion 81 away from the axis 54 in a direction toward the valve outlet port 36, results in a portion of the enlarged diameter portion 65 located generally opposite the valve outlet port 36 moving away from an internal wall 107 of the valve internal chamber 38. Fluid can then be introduced through the lumen 110 of the actuator 90 and into the internal valve chamber 38. Further, fluid is able to move between the enlarged diameter portion 65 of the rubber valve plug 14 and the wall 107 of the valve internal chamber 38 and, subsequently, into the valve outlet port 36. Thus, introduction of the actuator 90 through the valve inlet port 21 results in the establishment of a fluid flow path between the valve inlet port 21 and the valve outlet port 36.

The actuator 90 is inserted through both the valve inlet port 21 and the valve throat 23 against a bias of the metal or plastic spring 74. When the actuator 90 is removed from the valve inlet port 21, the spring 74 biases the elastomeric valve plug 14 back through the valve throat 23 and into the valve inlet 21. Curved guiding surfaces 118 help to facilitate this process of generally realigning the plug proximal portion 47 about the axis 54.

Introduction of the actuator 90 through the valve throat 23 and into the valve internal chamber 38 introduces a positive fluid displacement, which, if not compensated, results in an antegrade flow of fluid out of the valve outlet port 36. The slidable elastomeric valve plug 14 of the present invention is adapted for introducing a negative fluid displacement within the valve internal chamber 38, to thereby compensate for the positive fluid displacement introduced by the insertion of the male Luer nozzle 90. More particularly, as the elastomeric valve plug 14 is pushed in the direction of the plug distal portion 50 by the actuator 90, the plug cylindrical distal portion 70 is moved out of the valve internal chamber 38, to thereby generate a negative fluid displacement within the valve internal chamber 38. The plug cylindrical distal portion 70 is moved into the vented air chamber 43 to thereby effectively transfer the fluid displacement introduced by the actuator 90 into the ambient atmosphere.

Although the vented air chamber 43 is provided in fluid communication with the ambient atmosphere in the presently preferred embodiment, the air chamber 43 may, alternatively, be sealed. If the air chamber 43 is sealed, movement of the plug cylindrical distal portion 70 into a portion of the air chamber 43 results in compression of the gases within the air chamber 43 to thereby yield similar results.

Similarly, as the actuator 90 is removed from the valve inlet port 21, a negative fluid displacement is generated within the valve internal chamber 38 and the valve throat 23. The spring 74, however, biases the elastomeric valve plug 14 back into the valve inlet port 21 to thereby generate a positive or neutral fluid displacement within the valve internal chamber 38. The positive/neutral fluid displacement generated by movement of a portion of the elastomeric valve plug 14 back into the valve internal chamber 38 compensates for the negative fluid displacement generated by removal of the actuator 90 from the valve internal chamber 38. In the presently preferred embodiment, the diameter of the plug cylindrical distal portion 70 is configured to be approximately equal (or proportional) to the diameter of the actuator 90, to thereby yield very close compensating displacements between the two devices. If the diameters are changed, flushing can be achieved.

If the volume of the plug cylindrical distal portion 70 is slightly greater than the volume of the actuator 90, a small amount of retrograde flow will be created during insertion of the actuator 90 and, subsequently, antegrade (self-flushing) flow will be produced during removal of the actuator 90. This antegrade flow (self-flushing) produced during removal of the actuator 90 can be considered a desirable feature.

A first alternative embodiment of the present invention is illustrated in FIG. 3, where similar elements are numbered as in FIGS. 1 and 2, but preceded by a 3. In the alternative embodiment illustrated in FIG. 3, both the spring 74 and the plug cylindrical distal portion 70 are eliminated. The biasing force and valve return force of this embodiment are facilitated by a plug collapsible skirt 371, which is preferably integrally formed with the plug 314. The vented air chamber 343 is formed within the plug collapsible skirt 371 and the valve base 318. As the plug proximal portion 347 is pushed out of the valve throat 323 by an actuator (not shown), the plug collapsible skirt 371 is collapsed somewhat in a direction toward the valve base 318. As the plug collapsible skirt 371 is collapsed, air is displaced out of the vent aperture 344. This displacement of air through the vent aperture 344 compensates for displacement resulting from introduction of the actuator into the valve internal chamber 338. The configuration of FIG. 3 eliminates any potential problems which may be associated with the plug biased member 67 of FIG. 1.

Figure 5:
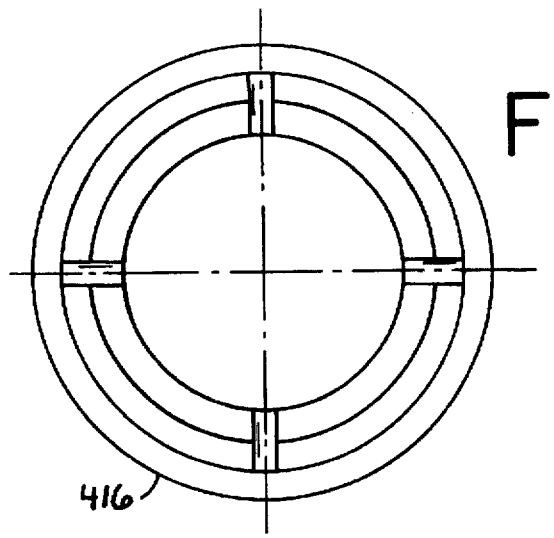
FIGS. 5 and 6 illustrate cross-sectional views of the minimum fluid displacement connector shown in FIG. 4.
Figure 6:
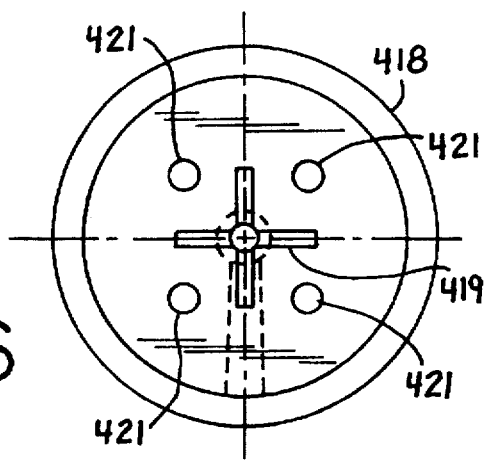

A second alternative embodiment is illustrated in FIGS. 4–6, where a spring 474 is provided within the plug collapsible skirt 471. Operation of this second alternative embodiment is similar to the operation of the embodiment of FIG. 3, with the exception of an additional biasing force facilitated by the spring 474. Another feature of the second alternative embodiment, which may be provided in any of the other embodiments of the present invention as well, is a distally located valve outlet port 436. An outlet port axis 485 of the valve outlet port 436 is substantially aligned with an axis 454 of the valve housing 412. The spring 474 of this embodiment may act as a rib cage to thereby limit the collapse of the plug collapsible skirt 471 under high fluid pressure.

The fluid path of this second alternative embodiment, when the system is actuated, is from the valve inlet port 421, through the valve throat 423, between the enlarged diameter portion 465 and the wall 407 of the valve internal chamber 438, through the U-shaped passage 466, and out of the valve outlet port 436. Air within the air chamber 443 may simply be compressed or, alternatively, may be vented to the ambient atmosphere upon actuation of the system. FIG. 5 illustrates a bottom view of the valve cap 416, and FIG. 6 illustrates a top view of the valve base 418. In the top view of the valve base 418, an internal strut 419 comprises an "X" configuration, and four vent ports 421 are provided for venting air from the air chamber 443 into the ambient atmosphere.

Figure 7:
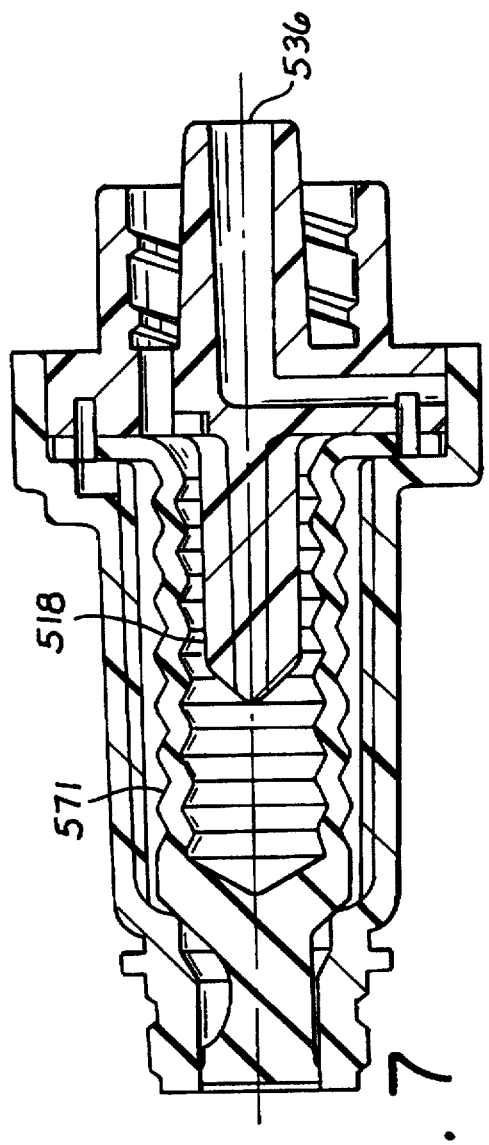
FIGS. 7 and 8 illustrate cross-sectional views of a minimum fluid displacement connector according a third alternative embodiment.
Figure 8:
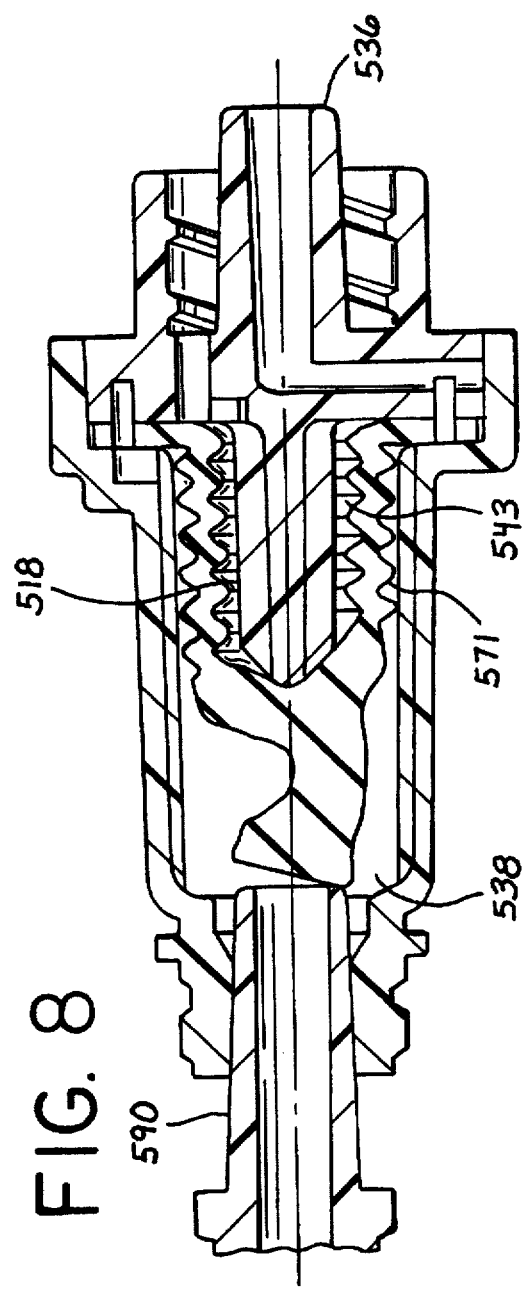

FIGS. 7 and 8 illustrate a third alternative embodiment of the present invention, which is similar to the embodiment of FIGS. 1 and 2. The third alternative embodiment of the present invention, however, comprises a plug collapsible skirt 571, an internal strut 518, and a distally located valve outlet port 536. As shown in FIG. 8, the internal strut 518 limits the collapse of the plug collapsible skirt 571 under high pressure. When the actuator 590 is inserted into the valve internal chamber 538 a positive fluid displacement is generated within the valve internal chamber 538. The plug collapsible skirt 571 collapses in a direction toward the valve outlet port 536 to thereby generate a compensating negative fluid displacement within the valve internal chamber 538. As the plug collapsible skirt 571 collapses and decreases the size of the air chamber 543, the air within the air chamber 543 is either compressed or vented to the ambient atmosphere.

Figure 9:
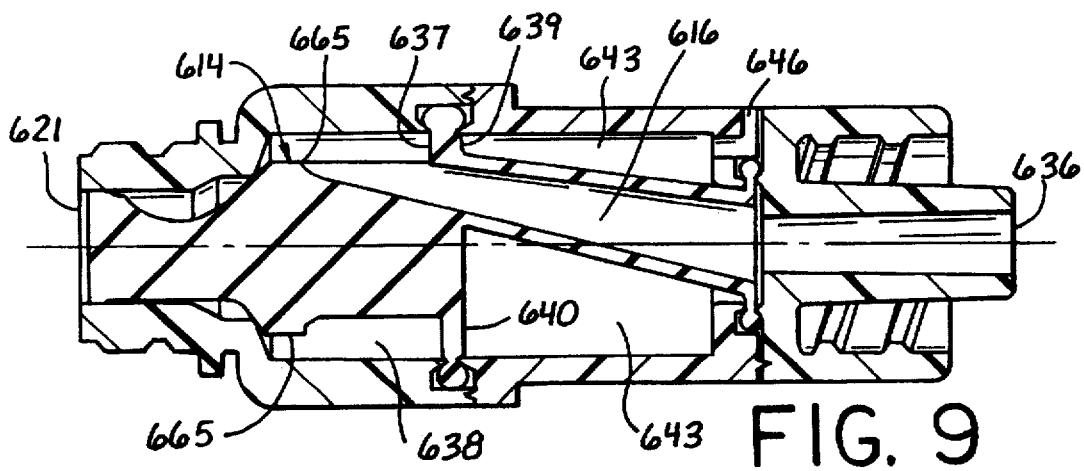
FIG. 9 illustrates a cross-sectional view of a minimum fluid displacement connector according to a fourth alternative embodiment of the present invention.

A fourth alternative embodiment of the present invention is illustrated in FIG. 9, where the rubber valve plug 614 comprises a plug hollow passage 616. The plug hollow passage 616 connects the valve outlet port 636 to the valve internal chamber 638. A valve vented air chamber 643 generally surrounds the plug hollow passage 616 of the rubber valve plug 614. When the device is actuated by insertion of an actuator (not shown) through the valve inlet port 621, the enlarged diameter portion 665 of the rubber valve plug 614 is moved generally in the direction of the valve outlet port 636. A plug annular member 637, however, resists this movement and provides return biasing action to the rubber valve plug 614 when the actuator is removed from the valve inlet port 621. The plug annular member 637 comprises thicker portions 639 and thinner portions 640. The thicker portions 639 provide stronger biasing effects than the thinner portions 640. As the actuator is inserted into the valve inlet port 621, the valve vented air chamber 643 contracts, as a result of the first and second portions 639 and 640 of the plug annular member 637, and the movement of the rubber valve plug 614 toward the valve outlet port 636. The positive fluid displacement introduced by insertion of the actuator through the valve inlet port 621 is thus countered by venting of air from the valve vented air chamber 643 through the vent aperture 646. The rubber valve plug 614 of this embodiment thus contains a plug hollow passage 616, which is somewhat centrally located and sealed from the valve vented air chamber 643 by assembled elements of the housing. These assembled elements of the housing may be joined by solvent bonding, ultrasonic welding, snap-fitting etc. As an alternative to using air in the valve vented air chamber 643, other gases may also be used. These other gases may be vented or compressible, as long as they facilitate compensating movement of the rubber valve plug 614 in response to insertion of the actuator into the device.

Although the above embodiments have been described in the context of medical devices, the principles of the present invention apply to any other valve connectors where it is desired to minimize fluid displacement as a result of valve actuation. Although exemplary embodiments of the invention have been shown and described, many other changes, modifications and substitutions, in addition to those set forth in the above paragraphs, may be made by one having ordinary skill in the art without necessarily departing from the spirit and scope of this invention.

We claim:

1. A minimum fluid displacement connector, comprising:
   a valve internal chamber having a proximal chamber end and a distal chamber end;
   a valve inlet port adapted for receiving an actuator, the actuator having a lumen for introducing fluid through the valve inlet port and into the valve internal chamber;
   a valve outlet port adapted for outputting fluid from the valve internal chamber, the valve outlet port being in fluid communication with the distal chamber end of the valve internal chamber at all times and being adapted for allowing fluid to freely flow into and out of the distal chamber end of the valve internal chamber through the valve outlet port;

an air chamber; and a plug adapted for being moved into a portion of the air chamber when the actuator is moved into the valve inlet port, movement of the plug into a portion of the air chamber resulting in a minimum displacement of fluid through the valve outlet port when the actuator is moved into the valve inlet port.

2. The minimum fluid displacement connector as recited in claim 1, the air chamber being in fluid communication with an ambient atmosphere, and movement of the plug into the air chamber resulting in movement of air out of the air chamber and into the ambient atmosphere.

3. The minimum fluid displacement connector as recited in claim 1, a displacement of air within the air chamber, resulting from movement of the plug into a portion of the air chamber, being approximately equal to or greater than a displacement of fluid within the valve internal chamber, resulting from movement of the actuator into the valve internal chamber.

4. The minimum fluid displacement connector as recited in claim 3, the valve inlet port having an inlet port axis, the air chamber being centered about the inlet port axis, the plug having a generally cylindrical shape which is also generally centered about the inlet port axis, and the plug being adapted for being moved from an inlet-port-closed position to an inlet-port-open position.

5. The minimum fluid displacement connector as recited in claim 4, the plug being adapted for being moved by the actuator from the inlet-port-closed position to the inlet-port-open position.

6. The minimum fluid displacement connector as recited in claim 5, the inlet-port-open position orienting a distal portion of the plug within a portion of the air chamber.

7. The minimum fluid displacement connector as recited in claim 6, the proximal portion of the plug being adapted for being pushed by the actuator from the inlet-port-closed position out of the valve inlet port and into the inlet-port-open position where the distal portion of the plug is positioned within a portion of the air chamber.

8. The minimum fluid displacement connector as recited in claim 7, further comprising a spring, the plug being adapted for being pushed by the spring from the inlet-port-open position back to the inlet-port-closed position.

9. The minimum fluid displacement connector as recited in claim 7, movement of the actuator into the valve internal chamber roughly corresponding to movement of the distal portion of the plug into a portion of the air chamber, the movement of the actuator into the valve internal chamber resulting in a displacement of fluid within the valve internal chamber that is compensated by movement of portions of the plug out of the valve internal chamber to thereby generate an approximately zero displacement within the valve internal chamber.

10. The minimum fluid displacement connector as recited in claim 9, the plug comprising a primary shoulder seal adapted for contacting a valve seat of the minimum fluid displacement connector when the plug is in the inlet-port-closed position, the primary shoulder seal being removed from contact with the valve seat when the plug is moved from the inlet-port-closed position to the inlet-port-open position.

11. The minimum fluid displacement connector as recited in claim 10, a first portion of the primary shoulder seal contacting an inner surface of the valve internal chamber when the plug is in the inlet-port-open position, and a second portion of the primary shoulder seal not contacting the inner surface of the valve internal chamber when the plug is in the inlet-port-open position.

12. The minimum fluid displacement connector as recited in claim 11, the inlet-port-open position of the plug facilitating a flow of fluid from the valve inlet port into the valve internal chamber, and between the second portion of the primary shoulder seal and the inner surface of the valve internal chamber into the valve outlet port, and out of the valve outlet port.

13. The minimum fluid displacement connector as recited in claim 9, a portion of the plug no longer being centered about the inlet port axis when the plug is in the inlet-port-open position, whereby fluid can pass from the valve inlet port, around a portion of the plug, and into the valve outlet port, when the plug is in the inlet-port-closed position.

14. The minimum fluid displacement connector as recited in claim 13, the valve outlet port having an outlet port axis that is substantially perpendicular to the inlet port axis.

15. The minimum fluid displacement connector as recited in claim 13, the valve outlet port having an outlet port axis that is substantially parallel to the inlet port axis.

16. A valve for transferring fluid with minimum fluid displacement, comprising:

a valve internal chamber having a proximal chamber end and a distal chamber end, and adapted for receiving an actuator therethrough for facilitating introduction of fluid into the valve internal chamber;

a biased member abutting against one of a compressible gas and an ambient atmosphere, and adapted for being moved by the actuator, movement of the biased member resulting in displacement of one of the compressible gas and the ambient atmosphere to offset a displacement of fluid in the valve internal chamber that was introduced by insertion of the actuator into the valve internal chamber; and a valve outlet port adapted for outputting fluid from the valve internal chamber, the valve outlet port being in fluid communication with the distal chamber end of the valve internal chamber at all times and being adapted for allowing fluid to freely flow between the distal chamber end of valve internal chamber and the valve outlet port.

17. A valve for transferring fluid, comprising:

an internal chamber that is in fluid communication with an outlet port, the internal chamber being adapted for accommodating an actuator therein, insertion of the actuator into the internal chamber placing the actuator into fluid communication with both the outlet port and substantially all of the internal chamber and resulting in a positive fluid displacement within the internal chamber and removal of the actuator from the internal chamber resulting in a negative fluid displacement within the internal chamber;

an air chamber; and a biased member adapted for being moved into a portion of the air chamber upon insertion of the actuator and for being moved out of a portion of the air chamber upon removal of the actuator, movement of the biased member into a portion of the air chamber resulting in a negative fluid displacement within the internal chamber which substantially compensates for the positive fluid displacement, and movement of the biased member out of a portion of the air chamber resulting in a positive fluid displacement within the internal chamber which substantially compensates for the negative fluid displacement, for a zero displacement within the internal chamber.

18. The valve as recited in claim 17, the biased member comprising a generally cylindrical member.

19. The valve as recited in claim 18, the generally cylindrical member comprising a hollow, collapsible skirt which surrounds and defines the air chamber, movement of the actuator into the internal chamber collapsing the collapsible skirt and moving the biased member into a portion of the air chamber.

20. The valve as recited in claim 19, further comprising a spring disposed within the collapsible skirt, movement of the actuator out of the internal chamber uncollapsing the collapsible skirt and moving the biased member out of a portion of the air chamber under forces exerted by the spring.

21. The valve as recited in claim 20, an axis of the internal chamber being substantially perpendicular to an axis of the outlet port.

22. The valve as recited in claim 20, an axis of the internal chamber being substantially parallel to an axis of the outlet port.

23. The valve as recited in claim 19, further comprising an internal strut disposed within the collapsible skirt, movement of the actuator into the internal chamber collapsing the collapsible skirt for a predetermined distance until a portion of the biased member contacts the internal strut.

24. The valve as recited in claim 17, the biased member comprising a hollow passage connecting the internal chamber to the outlet port, the hollow passage being surrounded by the air chamber and expanding into a portion of the air chamber when the actuator is inserted into the internal chamber, the hollow passage further contracting and moving out of a portion of the air chamber when the actuator is removed from the internal chamber.

25. The valve as recited in claim 17, the air chamber being in fluid communication with an ambient atmosphere, and movement of the biased member into a portion of the air chamber resulting in displacement of air within the air chamber out of the air chamber and into the ambient atmosphere.

26. The valve as recited in claim 17, the biased member further comprising an annular member adapted for being secured to a wall of the internal chamber, the annular member serving as a biasing means for contracting the hollow passage and moving the hollow passage out of the air chamber when the actuator is removed from the internal chamber.

27. A self-flushing connector, comprising:

a valve internal chamber;

a valve inlet port adapted for receiving an actuator, the actuator having a lumen for introducing fluid through the valve inlet port and into the valve internal chamber;

a valve outlet port adapted for outputting fluid from the valve internal chamber, the valve outlet port being in fluid communication with the valve internal chamber at all times and being adapted for allowing fluid to freely flow into and out of the valve internal chamber through the valve outlet port at all times;

an air chamber; and a plug adapted for being moved into a portion of the air chamber when the actuator is moved into the valve internal chamber and for being moved out of a portion of the air chamber when the actuator is removed from the valve internal chamber, movement of the actuator into the valve internal chamber resulting in a relatively small movement of fluid through the valve outlet port and into the valve internal chamber, and movement of the plug out of the valve internal chamber resulting in a relatively small movement of fluid through the valve outlet port and out of the valve internal chamber.

28. A self-flushing connector, comprising:

a valve inlet port adapted for receiving an actuator in an inward direction into the valve inlet port, the actuator having a lumen for introducing fluid through the valve inlet port in the inward direction;

a valve outlet port adapted for transferring fluid in one of a first direction out of the self-flushing connector and a second direction into the self-flushing connector; and displacing means adapted for providing displacements of fluid within the self-flushing connector, the displacing means effecting a relatively small movement of fluid through the valve outlet port in the second direction in response to movement of the actuator in the inward direction, and the displacing means effecting a relatively small movement of fluid through the valve outlet port in the first direction in response to movement of the actuator in an outward direction opposite to the inward direction.

29. A minimum fluid displacement connector, comprising:

a valve internal chamber;

a valve inlet port adapted for receiving an actuator, the actuator having a lumen for introducing fluid through the valve inlet port and into the valve internal chamber;

a valve outlet port adapted for outputting fluid from the valve internal chamber, the valve outlet port being in an unobstructed fluid communication with the valve internal chamber at all times and being adapted for allowing fluid to freely flow into and out of the valve internal chamber through the valve outlet port;

an air chamber; and a plug adapted for being moved into a portion of the air chamber when the actuator is moved into the valve inlet port, movement of the plug into a portion of the air chamber resulting in a minimum displacement of fluid through the valve outlet port when the actuator is moved into the valve inlet port.

30. A minimum fluid displacement connector, comprising:

a valve internal chamber having a volume;

a valve inlet port adapted for receiving an actuator, the actuator having a lumen for introducing fluid through the valve inlet port and into the valve internal chamber;

a valve outlet port adapted for outputting fluid from the valve internal chamber, the valve outlet port being in fluid communication with substantially all of the volume of the valve internal chamber at all times and being adapted for allowing fluid to freely flow into and out of substantially all of the volume of the valve internal chamber through the valve outlet port;

an air chamber; and a plug adapted for being moved into a portion of substantially all of the volume of the air chamber when the actuator is moved into the valve inlet port, movement of the plug into a portion of the air chamber resulting in a minimum displacement of fluid through the valve outlet port when the actuator is moved into the valve inlet port.

31. A valve for transferring fluid with minimum fluid displacement, comprising:

a valve internal chamber having a volume and adapted for receiving an actuator therethrough for facilitating introduction of fluid into the valve internal chamber;

a biased member abutting against one of a compressible gas and an ambient atmosphere, and adapted for being moved by the actuator, movement of the biased member resulting in displacement of one of the compressible gas and the ambient atmosphere to offset a displacement of fluid in the valve internal chamber that was introduced by insertion of the actuator into the valve internal chamber; and a valve outlet port adapted for outputting fluid from the valve internal chamber, the valve outlet port being in fluid communication with substantially all of the volume of the valve internal chamber at all times and being adapted for allowing fluid to freely flow between substantially all of the volume of the valve internal chamber and the valve outlet port.

32. A valve for transferring fluid with minimum fluid displacement, comprising:

a valve internal chamber adapted for receiving an actuator therethrough for facilitating introduction of fluid into the valve internal chamber;

a biased member abutting against one of a compressible gas and an ambient atmosphere, and adapted for being moved by the actuator, movement of the biased member resulting in displacement of one of the compressible gas and the ambient atmosphere to offset a displacement of fluid in the valve internal chamber that was introduced by insertion of the actuator into the valve internal chamber; and a valve outlet port adapted for outputting fluid from the valve internal chamber, the valve outlet port being in an unobstructed fluid communication with the valve internal chamber at all times and being adapted for allowing fluid to freely flow between the valve internal chamber and the valve outlet port at all times.

\* \* \* \* \*

UNITED STATES PATENT AND TRADEMARK OFFICE
CERTIFICATE OF CORRECTION

PATENT NO. : 5,730,418 C1
APPLICATION NO. : 90/006177
DATED : April 11, 2006
INVENTOR(S) : Feith et al.

It is certified that error appears in the above-identified patent and that said Letters Patent is hereby corrected as shown below:

Column 8, line 27, remove the "," between "A self-flushing connector" and "comprising"
Column 10, line 11, insert the word --out-- between "valve outlet port" and "of the self-flushing connector"
Column 10, line 48, insert the word --the-- between "is removed from" and "valve inlet port"

Signed and Sealed this

Twenty-fourth Day of August, 2010

David J. Kappos
*Director of the United States Patent and Trademark Office*

(12) EX PARTE REEXAMINATION CERTIFICATE (5331st)
United States Patent
Feith et al.

(10) Number: US 5,730,418 C1
(45) Certificate Issued: Apr. 11, 2006

(54) MINIMUM FLUID DISPLACEMENT MEDICAL CONNECTOR

(75) Inventors: Raymond P. Feith, Rialto, CA (US); David L. Ludwig, San Juan Capistrano, CA (US); Timothy L. Truitt, Orange, CA (US)

(73) Assignee: Porex Medical Products, Inc., Ontario, CA (US)

Reexamination Request:
No. 90/006,177, Dec. 27, 2001

Reexamination Certificate for:
Patent No.: 5,730,418
Issued: Mar. 24, 1998
Appl. No.: 08/724,180
Filed: Sep. 30, 1996

(51) Int. Cl.
*F16L 37/28* (2006.01)

(52) U.S. Cl. .............................. 251/149.6; 251/149.1; 604/256; 604/905
(58) Field of Classification Search .............. 251/149.6, 251/149.1; 604/256, 905
See application file for complete search history.

(56) References Cited
U.S. PATENT DOCUMENTS

| | | |
|---|---|---|
| 5,006,114 A | 4/1991 | Rogers et al. |
| 5,380,306 A | 1/1995 | Brinon |
| 5,417,673 A | 5/1995 | Gordon |
| 5,439,451 A | 8/1995 | Collinson et al. |
| 5,470,319 A | 11/1995 | Mayer |
| 5,577,706 A * | 11/1996 | King .................... 251/149.6 |
| 5,676,346 A | 10/1997 | Leinsing |

* cited by examiner

*Primary Examiner*—John Bastianelli

(57) ABSTRACT

A device for transferring fluid with minimum fluid displacement includes a valve internal chamber adapted for receiving an actuator therethrough for facilitating introduction of fluid into the valve internal chamber. A biased member abuts against either a compressible gas or an ambient atmosphere, and is adapted for being moved by the actuator. Movement of the biased member results in displacement of either the compressible gas or the ambient atmosphere to thereby offset a displacement of fluid in the valve internal chamber that was introduced by insertion of the actuator into the valve internal chamber. A valve outlet port is adapted for outputting fluid from the valve internal chamber. The valve outlet port is configured in fluid communication with the valve internal chamber at all times, and is adapted for allowing fluid to freely flow between the valve internal chamber and the valve outlet port.

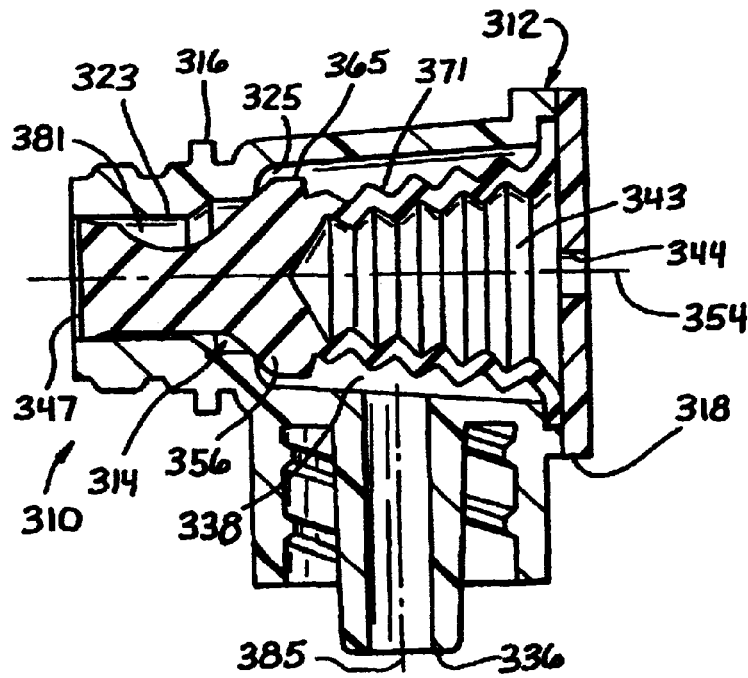

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 5, line 66 to column 6, line 22:

Turning to FIG. 2, an actuator 90 can be inserted into the valve inlet port 21 to thereby push the plug proximal portion 47 in the direction of the plug distal portion 50. *As shown in FIGS. 1 and 2, plug proximal portion 47 is not slitted, in contrast to prior art connectors having a slit septum. Accordingly, when actuator 90 is inserted, it enters the connector by displacing the plug proximal portion rather than by passing through a slit in the plug.* The actuator 90 comprises a male Luer nozzle in the presently preferred embodiment. The actuator 90 pushes the plug proximal portion 47 out of the valve throat 23 and, simultaneously, causes the plug proximal portion 47 to slightly rotate relative to the reduced diameter portion 81 in the clockwise direction, as presently embodied. This slight rotation of the plug proximal portion 47, coupled with a general migration of both the plug proximal portion 47 and the reduced diameter portion 81 away from the axis 54 in a direction toward the valve outlet port 36, results in a portion of the enlarged diameter portion 65 located generally opposite the valve outlet port 36 moving away from an internal wall 107 of the valve internal chamber 38. Fluid can then be introduced through the lumen 110 of the actuator 90 and into the internal valve chamber 38. Further, fluid is able to move between the enlarged diameter portion 65 of the rubber valve plug 14 and the wall 107 of the valve internal chamber 38 and, subsequently, into the valve outlet port 36. Thus, introduction of the actuator 90 through the valve inlet port 21 results in the establishment of a fluid flow path between the valve inlet port 21 and the valve outlet port 36.

Column 6, lines 31–47:

Introduction of the actuator 90 through the valve throat 23 and into the valve internal chamber 38 introduces a positive fluid displacement, which, if not compensated, results in an antegrade flow of fluid out of the valve outlet port 36. The slidable elastomeric valve plug 14 of the present invention is adapted for introducing a negative fluid displacement within the valve internal chamber 38, to thereby compensate for the positive fluid displacement introduced by the insertion of the male Luer nozzle 90. More particularly, as the elastomeric valve plug 14 is pushed in the direction of the plug distal portion 50 by the actuator 90, the plug cylindrical distal portion 70 is moved out of the valve internal chamber 38, to thereby generate a negative fluid displacement within the valve internal chamber 38. The plug cylindrical distal portion 70 is moved into the vented air chamber 43 to thereby effectively transfer the fluid displacement introduced by the actuator 90 into the ambient atmosphere. *As shown in FIGS. 1 and 2, plug 14 comprises a side surface that is exposed to fluid introduced into the valve internal chamber by actuator 90 and a distal portion 50 comprising a surface that is not exposed to fluid introduced into the valve internal chamber but is exposed to air chamber 43.*

Column 7, lines 13–32:

A first alternative embodiment of the present invention is illustrated in FIG. 3, where similar elements are numbered as in FIGS. 1 and 2, but preceded by a 3. *In contrast to the embodiment illustrated in FIGS. 1 and 2, where the biasing force and valve return force are provided by spring 74 and plug cylindrical distal portion 70 is not collapsible and moves into vented air chamber 43 to compensate for fluid displacement caused by introduction of the actuator into the valve internal chamber 38, in* the alternative embodiment illustrated in FIG. 3, both the spring 74 and the plug cylindrical distal portion 70 are eliminated. The biasing force and valve return force of this embodiment are facilitated by a plug collapsible skirt 371, which is preferably integrally formed with the plug 314. The vented air chamber 343 is formed within the plug collapsible skirt 371 and the valve base 318. As the plug proximal portion 347 is pushed out of the valve throat 323 by an actuator (not shown), the plug collapsible skirt 371 is collapsed somewhat in a direction toward the valve base 318. As the plug collapsible skirt 371 is collapsed, air is displaced out of the vent aperture 344. This displacement of air through the vent aperture 344 compensates for displacement resulting from introduction of the actuator into the valve internal chamber 338. The configuration of FIG. 3 eliminates any potential problems which may be associated with the plug biased member 67 of FIG. 1.

AS A RESULT OF REEXAMINATION, IT HAS BEEN DETERMINED THAT:

The patentability of claim 28 is confirmed.

Claims 1–3, 5, 6, 16–27 and 29–32 are determined to be patentable as amended.

Claims 4 and 7–15, dependent on an amended claim, are determined to be patentable.

New claims 33–77 are added and determined to be patentable.

1. A minimum fluid displacement connector, comprising:
a valve internal chamber having a proximal chamber end and a distal chamber end;
a valve inlet port adapted for receiving an actuator, the actuator having a lumen for introducing fluid through the valve inlet port and into the valve internal chamber;
a valve outlet port adapted for outputting fluid from the valve internal chamber, the valve outlet port being in fluid communication with the distal chamber end of the valve internal chamber at all times and being adapted for allowing fluid to freely flow into and out of the distal chamber end of the valve internal chamber through the valve outlet port;
*a valve housing with an inner surface that defines at least in part* an air chamber; and
a plug *with a proximal portion and a distal portion, the distal portion of the plug being non-collapsible, the*

*plug forming a slidable seal with the inner surface of the valve housing and being* adapted for [being moved into a portion of] *movement relative to* the air chamber when the actuator is moved into the valve inlet port, *the* movement of the plug [into a portion of] *relative to* the air chamber resulting in a minimum displacement of fluid through the valve outlet port when the actuator is moved into the valve inlet port.

2. The minimum fluid displacement connector as recited in claim 1, the air chamber being in fluid communication with an ambient atmosphere, and *the* movement of the *distal portion of the* plug into the air chamber resulting in movement of air out of the air chamber and into the ambient atmosphere.

3. The minimum fluid displacement connector as recited in claim 1, a displacement of air within the air chamber, resulting from *the* movement of the *distal portion of the* plug into a portion of the air chamber, being approximately equal to or greater than a displacement of fluid within the valve internal chamber, resulting from movement of the actuator into the valve internal chamber.

5. The minimum fluid displacement connector as recited in claim 4, the plug being adapted for being moved by the actuator from the inlet-port-closed position to the inlet-port-open position, *the proximal portion of the plug comprising a generally planar surface that is disposed in a non-perpendicular relationship with the inlet port axis when the plug is in the inlet-port-open position.*

6. The minimum fluid displacement connector as recited in claim 5, the inlet-port-open position orienting [a] *the* distal portion of the plug within a portion of the air chamber.

16. A valve for transferring fluid with minimum fluid displacement, comprising:

a valve housing having an inner surface;

a valve internal chamber *defined within the valve housing and* having a proximal chamber end and a distal chamber end, and adapted for receiving an actuator therethrough for facilitating introduction of fluid into the valve internal chamber;

a biased member abutting against one of a compressible gas and an ambient atmosphere, and adapted for being moved by the actuator, *the biased member comprising a non-slitted biased member proximal portion,* movement of the biased member resulting in displacement of one of the compressible gas and the ambient atmosphere to offset a displacement of fluid in the valve internal chamber that was introduced by insertion of the actuator into the valve internal chamber, *the biased member comprising a distal sealing member that slidably engages the inner surface of the valve housing*; and a valve outlet port adapted for outputting fluid from the valve internal chamber, the valve outlet port being in fluid communication with the distal chamber end of the valve internal chamber at all times and being adapted for allowing fluid to freely flow between the distal chamber end of valve internal chamber and the valve outlet port.

17. A valve for transferring fluid, comprising:

*an inlet port defining an axis;* an internal chamber that is in fluid communication with an outlet port, the internal chamber being adapted for accommodating an actuator therein, insertion of the actuator into the internal chamber placing the actuator into fluid communication with both the outlet port and substantially all of the internal chamber and resulting in a positive fluid displacement within the internal chamber and removal of the actuator from the internal chamber resulting in a negative fluid displacement within the internal chamber;

an air chamber; and a biased member adapted for being moved *from a first position* into a portion of the air chamber *to a second position* upon insertion of the actuator and for being moved *from the second position* out of a portion of the air chamber *to the first position* upon removal of the actuator, movement of the biased member [into a portion of the air chamber] *from the first position to the second position* resulting in a negative fluid displacement within the internal chamber which substantially compensates for the positive fluid displacement, and movement of the biased member [out of a portion of the air chamber] *from the second position to the first position* resulting in a positive fluid displacement within the internal chamber which substantially compensates for the negative fluid displacement, for a zero displacement within the internal chamber;

*wherein the biased member comprises a biased member proximal portion with a generally planar surface that is disposed in a non-perpendicular relationship with the axis when the biased member is in the second position.*

18. The valve as recited in claim 17, the biased member comprising *a biased member distal portion having* a generally cylindrical member.

21. The valve as recited in claim 20, [an] *the* axis of the [internal chamber] *inlet port* being substantially perpendicular to an axis of the outlet port.

22. The valve as recited in claim 20, [an] *the* axis of the [internal chamber] *inlet port* being substantially parallel to an axis of the outlet port.

24. The valve as recited in claim 17, the biased member [comprising] *defining in part* a hollow passage connecting the internal chamber to the outlet port, the hollow passage being surrounded by the air chamber and expanding into a portion of the air chamber when the actuator is inserted into the internal chamber, the hollow passage further contracting and moving out of a portion of the air chamber when the actuator is removed from the internal chamber.

26. The valve as recited in claim [17, the biased member] *24,* further comprising an annular member adapted for being secured to a wall of the internal chamber, the annular member serving as a biasing means for contracting the hollow passage and moving the hollow passage out of the air chamber when the actuator is removed from the internal chamber.

27. A self-flushing connector, comprising:

a valve internal chamber;

a valve inlet port adapted for receiving an actuator, the actuator having a lumen for introducing fluid through the valve inlet port and into the valve internal chamber;

a valve outlet port adapted for outputting fluid from the valve internal chamber, the valve outlet port being in fluid communication with the valve internal chamber at all times and being adapted for allowing fluid to freely flow into and out of the valve internal chamber through the valve outlet port at all times;

an air chamber; and a plug adapted for being moved into a portion of the air chamber when the actuator is moved into the valve internal chamber and for being moved out of a portion of the air chamber when the actuator is removed from the valve internal chamber, movement of the actuator into the valve internal chamber resulting in a relatively small movement of fluid through the valve outlet port and into the valve internal chamber, and movement of the [plug] *actuator* out of the valve internal chamber resulting in a relatively small movement of fluid through the valve outlet port and out of the valve internal chamber.

29. A minimum fluid displacement connector, comprising:

a valve internal chamber;

a valve inlet port adapted for receiving an actuator, the actuator having a lumen for introducing fluid through the valve inlet port and into the valve internal chamber;

a valve outlet port adapted for outputting fluid from the valve internal chamber, the valve outlet port being in an unobstructed fluid communication with the valve internal chamber at all times and being adapted for allowing fluid to freely flow into and out of the valve internal chamber through the valve outlet port;

*a valve housing having an inner surface that defines* an air chamber; and a plug *with a plug proximal portion and a non-collapsible plug distal portion, the non-collapsible plug distal portion having a slidable seal that engages the inner surface of the valve housing, the non-collapsible plug distal portion* adapted for being moved into a portion of the air chamber when the actuator is moved into the valve inlet port, movement of the *non-collapsible* plug *distal portion* into a portion of the air chamber resulting in a minimum displacement of fluid through the valve outlet port when the actuator is moved into the valve inlet port.

30. A minimum fluid displacement connector, comprising:

a valve internal chamber having a volume;

a valve inlet port adapted for receiving an actuator, the actuator having a lumen for introducing fluid through the valve inlet port and into the valve internal chamber;

a valve outlet port adapted for outputting fluid from the valve internal chamber, the valve outlet port being in fluid communication with substantially all of the volume of the valve internal chamber at all times and being adapted for allowing fluid to freely flow into and out of substantially all of the volume of the valve internal chamber through the valve outlet port;

an air chamber *defined at least in part by a distal cylinder of a valve housing*; and a *non-slitted* plug adapted for being moved into a portion of substantially all of the volume of the air chamber when the actuator is moved into the valve inlet port, movement of the plug into a portion of the air chamber resulting in a minimum displacement of fluid through the valve outlet port when the actuator is moved into the valve inlet port.

31. A valve for transferring fluid with minimum fluid displacement, comprising:

a valve internal chamber having a volume and adapted for receiving an actuator therethrough for facilitating introduction of fluid into the valve internal chamber;

a biased member abutting against one of a compressible gas and an ambient atmosphere, and adapted for being moved by the actuator, movement of the biased member resulting in displacement of one of the compressible gas and the ambient atmosphere to [offset] *overcompensate* a displacement of fluid in the valve internal chamber that was introduced by insertion of the actuator into the valve internal chamber; and a valve outlet port adapted for outputting fluid from the valve internal chamber, the valve outlet port being in fluid communication with substantially all of the volume of the valve internal chamber at all times and being adapted for allowing fluid to freely flow between substantially all of the volume of the valve internal chamber and the valve outlet port.

32. A valve for transferring fluid with minimum fluid displacement, comprising:

a valve internal chamber adapted for receiving an actuator therethrough for facilitating introduction of fluid into the valve internal chamber;

a biased member abutting against one of a compressible gas and an ambient atmosphere, and adapted for being moved by the actuator, movement of the biased member resulting in displacement of one of the compressible gas and the ambient atmosphere to offset a displacement of fluid in the valve internal chamber that was introduced by insertion of the actuator into the valve internal chamber, *the biased member having a generally planar surface adapted for being abutted by the actuator, the generally planar surface being oriented in a slanted relationship with respect to an end surface of the actuator when the actuator is inserted into the valve internal chamber*; and a valve outlet port adapted for outputting fluid from the valve internal chamber, the valve outlet port being in an unobstructed fluid communication with the valve internal chamber at all times and being adapted for allowing fluid to freely flow between the valve internal chamber and the valve outlet port at all times.

*33. The minimum fluid displacement connector as recited in claim 4, the valve outlet port having an outlet port axis that is substantially perpendicular to the inlet port axis.*

*34. The valve as recited in claim 16, the biased member comprising a biased member proximal portion and a biased member distal portion.*

*35. The valve as recited in claim 34, the biased member proximal portion comprising a reduced diameter portion, the biased member proximal portion being pivotable about the reduced diameter portion.*

*36. The valve as recited in claim 35, the biased member distal portion being non-collapsible.*

*37. The valve as recited in claim 17, the biased member proximal portion facilitating a seal of the internal chamber when the biased member proximal portion is in the first position.*

*38. The valve as recited in claim 17, the planar surface being in a perpendicular relationship with the axis when the biased member proximal portion is in the first position.*

*39. The self-flushing connector as recited in claim 27, the plug comprising a planar surface adapted for being abutted by the actuator.*

*40. The self-flushing connector as recited in claim 39, wherein:*

*the valve inlet port defines an axis; and*

*when the actuator is moved into the valve internal chamber, the planar surface is disposed in a non-perpendicular relationship with the axis.*

*41. The self-flushing connector as recited in claim 39, wherein:*

*the valve inlet port defines an inlet port axis; and*

*the valve outlet port defines an outlet port axis that is substantially perpendicular to the valve inlet port axis.*

*42. The self-flushing connector as recited in claim 28, wherein:* the valve inlet port defines an inlet port axis; and the valve outlet port defines an outlet port axis that is substantially perpendicular to the valve inlet port axis.

43. The minimum fluid displacement connector as recited in claim 29, wherein:

the valve inlet port defines an inlet port axis; and the valve outlet port defines an outlet port axis that is substantially perpendicular to the valve inlet port axis.

44. The minimum fluid displacement connector as recited in claim 29, the valve outlet port being substantially parallel to the valve inlet port.

45. The minimum fluid displacement connector as recited in claim 30, wherein:

the valve inlet port defines an inlet port axis; and the valve outlet port defines an outlet port axis that is substantially perpendicular to the valve inlet port axis.

46. The minimum fluid displacement connector as recited in claim 30, the plug comprising a distal sealing member that slidably seals the air chamber from the valve internal chamber.

47. The valve as recited in claim 31, the biased member comprising a biased member distal portion that translates into one of the compressible gas and the ambient atmosphere when the actuator is inserted into the valve internal chamber.

48. A minimum fluid displacement connector, comprising:

a valve internal chamber having a proximal chamber end and a distal chamber end;

a valve inlet port adapted for receiving an actuator, the actuator having a lumen for introducing fluid through the valve inlet port and into the valve internal chamber, the valve inlet port defining an axis;

a valve outlet port adapted for outputting fluid from the valve internal chamber, the valve outlet port being in fluid communication with the distal chamber end of the valve internal chamber at all times and being adapted for allowing fluid to freely flow into and out of the distal chamber end of the valve internal chamber through the valve outlet port;

an air chamber; and a plug having a plug proximal portion and a non-collapsible plug distal portion, the plug proximal portion being adapted for movement between a first position, when the actuator is not inserted in the inlet port, and a second position, when the actuator is inserted into the inlet port, the non-collapsible plug distal portion being adapted for being moved into a portion of the air chamber when the actuator is moved into the valve inlet port, wherein the plug proximal portion comprises a generally planar surface adapted for being abutted by the actuator, the generally planar surface being disposed in a non-perpendicular relationship with the axis when the plug proximal portion is in the second position, and wherein movement of the non-collapsible plug distal portion into a portion of the air chamber results in a minimum displacement of fluid through the valve outlet port when the actuator is moved into the valve inlet port.

49. The connector as recited in claim 48, the plug distal portion comprising an annular sealing member.

50. The connector as recited in claim 48, the outlet port being substantially perpendicular to the inlet port.

51. The connector as recited in claim 48, the outlet port being substantially parallel to the inlet port.

52. A minimum fluid displacement connector, comprising:

a valve internal chamber having a proximal chamber end and a distal chamber end;

a valve inlet port adapted for receiving an actuator, the actuator having a lumen for introducing fluid through the valve inlet port and into the valve internal chamber;

a valve outlet port adapted for outputting fluid from the valve internal chamber, the valve outlet port being in fluid communication with the distal chamber end of the valve internal chamber at all times and being adapted for allowing fluid to freely flow into and out of the distal chamber end of the valve internal chamber through the valve outlet port;

an air chamber; and a plug adapted for being moved into a portion of the air chamber when the actuator is moved into the valve inlet port, movement of the plug into a portion of the air chamber resulting in a minimum displacement of fluid through the valve outlet port when the actuator is moved into the valve inlet port;

the plug comprising a side surface that is exposed to fluid introduced into the valve internal chamber by the actuator and a non-collapsible distal portion comprising a surface that is not exposed to fluid introduced into the valve internal chamber by the actuator but is exposed to the air chamber.

53. A self-flushing connector, comprising:

a valve internal chamber;

a valve inlet port adapted for receiving an actuator, the actuator having a lumen for introducing fluid through the valve inlet port and into the valve internal chamber;

a valve outlet port adapted for outputting fluid from the valve internal chamber, the valve outlet port being in fluid communication with the valve internal chamber at all times and being adapted for allowing fluid to freely flow into and out of the valve internal chamber through the valve outlet port at all times;

an air chamber; and a plug adapted for being moved into a portion of the air chamber when the actuator is moved into the valve internal chamber and for being moved out of a portion of the air chamber when the actuator is removed from the valve internal chamber, movement of the actuator into the valve internal chamber resulting in a relatively small movement of fluid through the valve outlet port and into the valve internal chamber, and movement of the plug out of the valve internal chamber resulting in a relatively small movement of fluid through the valve outlet port and out of the valve internal chamber;

the plug comprising a side surface that is exposed to fluid introduced into the valve internal chamber by the actuator and a non-collapsible distal portion comprising a surface that is not exposed to fluid introduced into the valve internal chamber by the actuator but is exposed to the air chamber.

54. The self-flushing connector as recited in claim 28 wherein the displacing means includes a non-slitted plug.

55. The self-flushing connector as recited in claim 28 wherein the displacing means includes a plug separating an air chamber from a valve internal chamber in fluid communication with the valve outlet port.

56. The self-flushing connector as recited in claim 55 wherein the plug includes a collapsible skirt defining the air chamber within the collapsible skirt.

57. The self-flushing connector as recited in claim 56 further comprising a spring, the plug adapted for being pushed by the spring from an inlet-port-open position back to an inlet-port-closed position.

58. The self-flushing connector as recited in claim 56 wherein the air chamber generally surrounds a plug hollow passage forming a part of the valve internal passage.

59. The self-flushing connector as recited in claim 28 wherein the displacing means includes an air chamber and a plug adapted for being moved into a portion of the air chamber when the actuator is moved into the valve inlet port.

60. The self-flushing connector as recited in claim 28 wherein the self-flushing connector includes a valve internal chamber in fluid connection with the valve inlet port and the displacing means includes a plug having a collapsible skirt defining an air chamber, the plug being moved into a portion of the air chamber when the actuator is moved into the valve inlet port.

61. The self-flushing connector as recited in claim 27, a displacement of air within the air chamber, resulting from movement of the plug into a portion of the air chamber, being approximately equal to or greater than a displacement of fluid within the valve internal chamber, resulting from movement of the actuator into the valve internal chamber.

62. The self-flushing connector as recited in claim 27, the valve inlet port having an inlet port axis, the air chamber being centered about the inlet port axis, the plug having a generally cylindrical shape which is also generally centered about the inlet port axis, and the plug being adapted for being moved from an inlet-port-closed position to an inlet-port-open position.

63. The self-flushing connector as recited in claim 62, further comprising a spring, the plug being adapted for being pushed by the spring from the inlet-port-open position back to the inlet-port-closed position.

64. The self-flushing connector as recited in claim 27, the plug comprising a primary shoulder seal adapted for contacting a valve seat of the self-flushing connector when the plug is in the inlet-port-closed position, the primary shoulder seal being removed from contact with the valve seat when the plug is moved from an inlet-port-closed position to an inlet-port-open position.

65. The self-flushing connector as recited in claim 27, the plug including a hollow, collapsible skirt which surrounds and defines the air chamber, movement of the actuator into the internal chamber collapsing the collapsible skirt.

66. The self-flushing connector as recited in claim 27, the plug including a hollow passage connecting the internal chamber to the outlet port, the hollow passage being surrounded by the air chamber and expanding into a portion of the air chamber when the actuator is moved into the internal chamber, the hollow passage further contracting and moving out of a portion of the air chamber when the actuator is removed from the internal chamber.

67. The self-flushing connector as recited in claim 27, wherein the plug has a proximal portion adapted for being pushed by the actuator from the inlet-port-closed position into the inlet-port-open position and the plug further has an enlarged diameter portion located in the valve internal chamber when the plug is in the inlet-port-closed position.

68. A self-flushing connector, comprising:
 a valve internal chamber having a proximal chamber end and a distal chamber end;
 a valve inlet port adapted for receiving an actuator, the actuator having a lumen for introducing fluid through the valve inlet port and into the valve internal chamber;
 a valve outlet port adapted for outputting fluid from the valve internal chamber, the valve outlet port being in fluid communication with the distal chamber end of the valve internal chamber at all times and being adapted for allowing fluid to freely flow into and out of the distal chamber end of the valve internal chamber through the valve outlet port;
 an air chamber; and
 a plug adapted for being moved into a portion of the air chamber when the actuator is moved into the valve inlet port, movement of the plug into a portion of the air chamber resulting in a minimum displacement of fluid through the valve outlet port into the self-flushing connector when the actuator is moved into the valve inlet port and a minimum displacement of fluid through the valve outlet port of the self-flushing connector when an actuator is moved out of the valve inlet port.

69. The self-flushing connector as recited in claim 68, a displacement of air within the air chamber, resulting from movement of the plug into a portion of the air chamber, being approximately equal to a displacement of fluid within the valve internal chamber, resulting from movement of the actuator into the valve inlet port.

70. The self-flushing connector as recited in claim 68, the valve inlet port having an inlet port axis, the air chamber being centered about the inlet port axis, the plug having a generally cylindrical shape which is also generally centered about the inlet port axis, and the plug being adapted for being moved from an inlet-port-closed position to an inlet-port-open position.

71. The self-flushing connector as recited in claim 70, further comprising a spring, the plug being adapted for being pushed by the spring from the inlet-port-open position back to the inlet-port-closed position.

72. The self-flushing connector as recited in claim 68, the plug comprising a primary shoulder seal adapted for contacting a valve seat of the self-flushing connector when the plug is in the inlet-port-closed position, the primary shoulder seal being removed from contact with the valve seat when the plug is moved from an inlet-port-closed position to an inlet-port-open position.

73. The self-flushing connector as recited in claim 68, the plug including a hollow, collapsible skirt which surrounds and defines the air chamber, movement of the actuator into the internal chamber collapsing the collapsible skirt.

74. The self-flushing connector as recited in claim 68, the plug including a hollow passage connecting the internal chamber to the valve outlet port, the hollow passage being surrounded by the air chamber and expanding into a portion of the air chamber when the actuator is inserted into the valve inlet port, the hollow passage further contracting and moving out of a portion of the air chamber when the actuator is removed from valve inlet port.

75. The self-flushing connector as recited in claim 68, wherein the plug has a proximal portion adapted for being pushed by the actuator from the inlet-port-closed position into the inlet-port-open position and the plug further has an enlarged diameter portion located in the valve internal chamber when the plug is in the inlet-port-closed position.

76. The self-flushing connector as recited in claim 70, the plug comprising a primary shoulder seal adapted for contacting a valve seat of the self-flushing connector when the plug is in the inlet-port-closed position, the primary shoulder seal being removed from contact with the valve seat when the plug is moved from an inlet-port-closed position to an inlet-port-open position.

77. The self-flushing connector as recited in claim 76, wherein the plug has a proximal portion adapted for being pushed by the actuator from the inlet-port-closed position into the inlet-port-open position and the plug further has an enlarged diameter portion located in the valve internal chamber when the plug is in the inlet-port-closed position.

* * * * *